US009147041B2

(12) United States Patent
Amarasingham et al.

(10) Patent No.: US 9,147,041 B2
(45) Date of Patent: Sep. 29, 2015

(54) CLINICAL DASHBOARD USER INTERFACE SYSTEM AND METHOD

(71) Applicant: Parkland Center for Clinical Innovation, Dallas, TX (US)

(72) Inventors: Rubendran Amarasingham, Dallas, TX (US); Timothy S. Swanson, Grapevine, TX (US); Sambamurthy Nalla, Flower Mound, TX (US); Yu Qian, San Diego, CA (US); George R. Oliver, Southlake, TX (US); Kimberly P. Gerra, Keller, TX (US)

(73) Assignee: Parkland Center for Clinical Innovation, Dallas, TX (US)

( * ) Notice: Subject to any disclaimer, the term of this patent is extended or adjusted under 35 U.S.C. 154(b) by 226 days.

(21) Appl. No.: 14/018,514

(22) Filed: Sep. 5, 2013

(65) Prior Publication Data
US 2014/0074509 A1    Mar. 13, 2014

Related U.S. Application Data

(63) Continuation-in-part of application No. 13/613,980, filed on Sep. 13, 2012.

(60) Provisional application No. 61/700,557, filed on Sep. 13, 2012.

(51) Int. Cl.
| G06F 15/18 | (2006.01) |
| G06E 1/00 | (2006.01) |
| G06E 3/00 | (2006.01) |
| G06G 7/00 | (2006.01) |
| G06F 19/00 | (2011.01) |

(52) U.S. Cl.
CPC ............ *G06F 19/322* (2013.01); *G06F 19/345* (2013.01); *G06F 19/3431* (2013.01); *G06F 19/3443* (2013.01)

(58) Field of Classification Search
USPC .......................................... 706/21
See application file for complete search history.

(56) References Cited

U.S. PATENT DOCUMENTS

| 8,241,642 B2 * | 8/2012 | Zagursky et al. | 424/244.1 |
| 8,293,489 B2 * | 10/2012 | Henkin | 435/7.21 |
| 8,506,934 B2 * | 8/2013 | Henkin | 424/10.1 |

(Continued)

OTHER PUBLICATIONS

Wearable Wireless Sensor Network to Assess Clinical Status in Patients with Neurological Disorders, Lorincz, K.; Kuris, B.; Ayer, S.M.; Patel, S.; Bonato, P.; Welsh, M. Information Processing in Sensor Networks, 2007. IPSN 2007. 6th International Symposium on Year: 2007 pp. 563-564, DOI: 10.1109/IPSN.2007.4379727.*

(Continued)

*Primary Examiner* — Michael B Holmes
(74) *Attorney, Agent, or Firm* — Wei Wei Jeang; Grable Martin Fulton PLLC

(57) ABSTRACT

A dashboard user interface method comprises displaying a navigable list of at least one target disease, displaying a navigable list of patient identifiers associated with a target disease selected in the target disease list, displaying historic and current data associated with a patient in the patient list identified as being associated with the selected target disease, including clinician notes at admission, receiving, storing, and displaying review's comments, and displaying automatically-generated intervention and treatment recommendations.

22 Claims, 10 Drawing Sheets

(56) References Cited

U.S. PATENT DOCUMENTS

| | | | |
|---|---|---|---|
| 8,663,938 B2* | 3/2014 | Henkin | 435/7.21 |
| 8,859,004 B2* | 10/2014 | Zhang et al. | 424/491 |
| 8,968,706 B2* | 3/2015 | Henkin | 424/10.1 |
| 2013/0034589 A1* | 2/2013 | Zhang et al. | 424/400 |
| 2013/0262357 A1* | 10/2013 | Amarasingham et al. | 706/21 |
| 2014/0074509 A1* | 3/2014 | Amarasingham et al. | 705/3 |
| 2015/0025329 A1* | 1/2015 | Amarasingham et al. | 600/301 |
| 2015/0106123 A1* | 4/2015 | Amarasingham et al. | 705/3 |

OTHER PUBLICATIONS

Early detection and characterization of Alzheimer's disease in clinical scenarios using Bioprofile concepts and K-means Escudero, J.; Zajicek, J.P.; Ifeachor, E. Engineering in Medicine and Biology Society, EMBC, 2011 Annual International Conference of the IEEE Year: 2011 pp. 6470-6473, DOI: 10.1109/IEMBS.2011.6091597.*

Re: Mind: A mobile application for bipolar disorder patients, Festersen, P.L.; Corradini, A. Wireless Mobile Communication and Healthcare (Mobihealth), 2014 EAI 4th International Conference on Year: 2014 pp. 343-346, DOI: 10.1109/MOBIHEALTH.2014.7015981.*

Predictive monitoring for early detection of subacute potentially catastrophic illnesses in critical care, Moorman, J.R.; Rusin, C.E.; Hoshik Lee; Guin, L.E.; Clark, M.T.; Delos, J.B.; Kattwinkel, J.; Lake, D.E. Engineering in Medicine and Biology Society, Annual Intl Conf of the IEEE Year: 2011 pp. 5515-5518, DOI: 10.1109/IEMBS.2011.6091407.*

* cited by examiner

FIG. 8

CLINICAL DASHBOARD USER INTERFACE SYSTEM AND METHOD

RELATED APPLICATION

This patent application claims the benefit of U.S. Provisional Application No. 61/700,557 entitled "Dashboard User Interface System and Method" filed on Sep. 13, 2012, and is a continuation-in-part application of U.S. Non-Provisional application Ser. No. 13/613,980 entitled "Clinical Predictive and Monitoring System and Method" filed on Sep. 13, 2012, which claims the benefit of U.S. Provisional Patent Application No. 61/552,525 entitled "Clinical Predictive and Monitoring System and Method" filed on Oct. 28, 2011, and U.S. Provisional Application No. 61/700,557 entitled "Dashboard User Interface System and Method" filed on Sep. 13, 2012. All afore-mentioned patent applications are herein incorporated by reference.

FIELD

The present disclosure relates to a clinical dashboard user interface system and method, and in particular in the field of disease identification and monitoring.

BACKGROUND

One of the challenges facing hospitals today is identifying a patient's primary illness as early as possible, so that appropriate interventions can be deployed immediately. Some illnesses, such as Acute Myocardial Infarction (AMI) and pneumonia, require an immediate standard action or pathway within 24 hours of the diagnosis. Other illnesses are less acute but still require careful adherence to medium and long-term treatment plans over multiple care settings.

The Joint Commission, the hospital accreditation agency approved by the Centers for Medicare and Medicaid Services (CMS), has developed Core Measures that have clearly articulated process measures. These measures are tied to standards that could result in CMS penalties for poor performance. For example, the measures set forth for Acute Myocardial Infarction include:

| Set Measure ID # | Measure Short Name |
|---|---|
| AMI-1 | Aspirin at Arrival |
| AMI-2 | Aspirin Prescribed at Discharge |
| AMI-3 | ACEI or ARB for LVSD |
| AMI-4 | Adult Smoking Cessation Advice/Counseling |
| AMI-5 | Beta-Blocker Prescribed at Discharge |
| AMI-7 | Median Time to Fibrionolysis |
| AMI-7a | Fibrinolytic Therapy Received within 30 minutes of Hospital Arrival |
| AMI-8 | Median Time to Primary PCI |
| AMI-8a | Primary PCI Received within 90 minutes of Hospital Arrival |
| AMI-9 | Inpatient Mortality (retired effective Dec. 31, 2010) |
| AMI-10 | Statin Prescribed at Discharge |

To date, most reporting and monitoring of accountable measure activities are done after the patient has been discharged from the healthcare facility. The delay in identifying and learning about a particular intervention often makes it impossible to rectify any situation. It is also difficult for a hospital administrator to determine how well the hospital is meeting core measures on a daily basis. Clinicians need a real-time or near real-time view of patient progress and care throughout the hospital stay, including clinician notes, that will inform actions (pathways and monitoring) on the part of care management teams and physicians toward meeting these core measures.

Case management teams have difficulty following patients' real-time disease status. The ability to do this with a clear picture of clinician's notes as they change in real-time as new information comes in during a patient's hospital stay would increase the teams' ability to apply focused interventions as early as possible and follow or change those pathways as needed throughout a patient's hospital stay, increasing quality and safety of care, decreasing unplanned readmissions and adverse events, and improving patient outcomes. This disclosure describes software developed to identify and risk stratify patients at highest risk for hospital readmissions and other adverse clinical events, and a dashboard user interface that presents data to the users in a clear and easy-to-understand manner.

BRIEF DESCRIPTION OF THE DRAWINGS

FIG. 8 is an exemplary screen shot of a dashboard user interface system and method according to the present disclosure;

DETAILED DESCRIPTION

Figure 1:
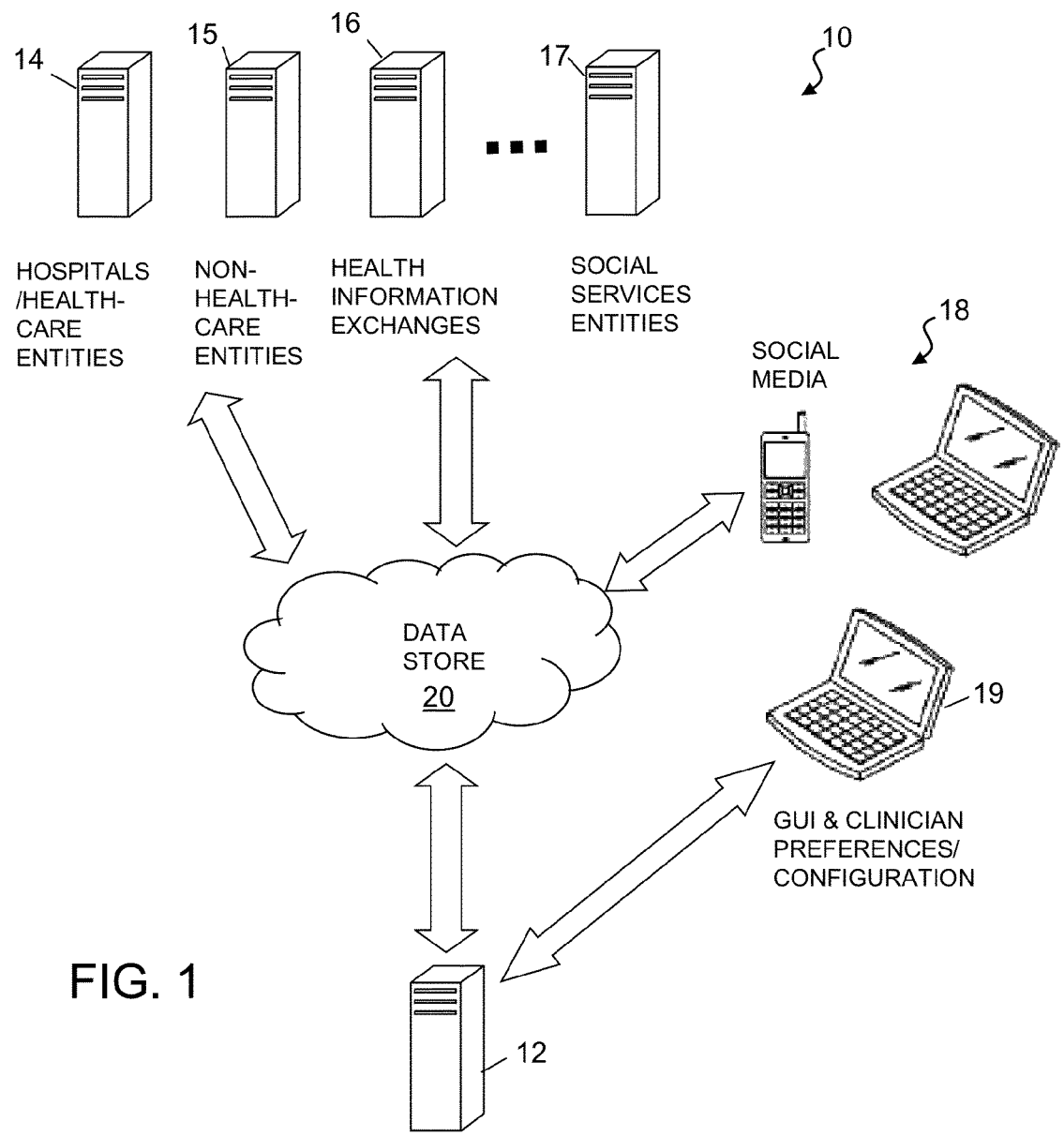
FIG. 1 is a simplified block diagram of an exemplary embodiment of a clinical predictive and monitoring system and method according to the present disclosure.

FIG. 1 is a simplified block diagram of an exemplary embodiment of a clinical predictive and monitoring system 10 according to the present disclosure. The clinical predictive and monitoring system 10 includes a computer system 12 adapted to receive a variety of clinical and non-clinical data relating to patients or individuals requiring care. The variety of data include real-time data streams and historical or stored data from hospitals and healthcare entities 14, non-health care entities 15, health information exchanges 16, and social-to-health information exchanges and social services entities 17, for example. These data are used to determine a disease risk score for selected patients so that they may receive more target intervention, treatment, and care that are better tailored and customized to their particular condition and needs. The system 10 is most suited for identifying particular patients who require intensive inpatient and/or outpatient care to avert serious detrimental effects of certain diseases and to reduce hospital readmission rates. It should be noted that the computer system 12 may comprise one or more local or remote computer servers operable to transmit data and communicate via wired and wireless communication links and computer networks.

The data received by the clinical predictive and monitoring system 10 may include electronic medical records (EMR) that include both clinical and non-clinical data. The EMR clinical data may be received from entities such as hospitals, clinics, pharmacies, laboratories, and health information exchanges, including: vital signs and other physiological data; data associated with comprehensive or focused history and physical exams by a physician, nurse, or allied health professional; medical history; prior allergy and adverse medical reactions; family medical history; prior surgical history; emergency room records; medication administration records; culture results; dictated clinical notes and records; gynecological and obstetric history; mental status examination; vaccination records; radiological imaging exams; invasive visualization procedures; psychiatric treatment history; prior histological specimens; laboratory data; genetic information; physician's notes; networked devices and monitors (such as blood pressure devices and glucose meters); pharmaceutical and supplement intake information; and focused genotype testing.

The EMR non-clinical data may include, for example, social, behavioral, lifestyle, and economic data; type and nature of employment; job history; medical insurance information; hospital utilization patterns; exercise information; addictive substance use; occupational chemical exposure; frequency of physician or health system contact; location and frequency of habitation changes; predictive screening health questionnaires such as the patient health questionnaire (PHQ); personality tests; census and demographic data; neighborhood environments; diet; gender; marital status; education; proximity and number of family or care-giving assistants; address; housing status; social media data; and educational level. The non-clinical patient data may further include data entered by the patients, such as data entered or uploaded to a social media website.

Additional sources or devices of EMR data may provide, for example, lab results, medication assignments and changes, EKG results, radiology notes, daily weight readings, and daily blood sugar testing results. These data sources may be from different areas of the hospital, clinics, patient care facilities, patient home monitoring devices, among other available clinical or healthcare sources.

As shown in FIG. 1, patient data sources may include non-healthcare entities 15. These are entities or organizations that are not thought of as traditional healthcare providers. These entities 15 may provide non-clinical data that include, for example, gender; marital status; education; community and religious organizational involvement; proximity and number of family or care-giving assistants; address; census tract location and census reported socioeconomic data for the tract; housing status; number of housing address changes; frequency of housing address changes; requirements for governmental living assistance; ability to make and keep medical appointments; independence on activities of daily living; hours of seeking medical assistance; location of seeking medical services; sensory impairments; cognitive impairments; mobility impairments; educational level; employment; and economic status in absolute and relative terms to the local and national distributions of income; climate data; and health registries. Such data sources may provide further insightful information about patient lifestyle, such as the number of family members, relationship status, individuals who might help care for a patient, and health and lifestyle preferences that could influence health outcomes.

The clinical predictive and monitoring system 10 may further receive data from health information exchanges (HIE) 16. HIEs are organizations that mobilize healthcare information electronically across organizations within a region, community or hospital system. HIEs are increasingly developed to share clinical and non-clinical patient data between healthcare entities within cities, states, regions, or within umbrella health systems. Data may arise from numerous sources such as hospitals, clinics, consumers, payers, physicians, labs, outpatient pharmacies, ambulatory centers, nursing homes, and state or public health agencies.

A subset of HIEs connect healthcare entities to community organizations that do not specifically provide health services, such as non-governmental charitable organizations, social service agencies, and city agencies. The clinical predictive and monitoring system 10 may receive data from these social services organizations and social-to-health information exchanges 17, which may include, for example, information on daily living skills, availability of transportation to doctor appointments, employment assistance, training, substance abuse rehabilitation, counseling or detoxification, rent and utilities assistance, homeless status and receipt of services, medical follow-up, mental health services, meals and nutrition, food pantry services, housing assistance, temporary shelter, home health visits, domestic violence, appointment adherence, discharge instructions, prescriptions, medication instructions, neighborhood status, and ability to track referrals and appointments.

Another source of data include social media or social network services 18, such as FACEBOOK and GOOGLE+ websites. Such sources can provide information such as the number of family members, relationship status, identify individuals who may help care for a patient, and health and lifestyle preferences that may influence health outcomes. These social media data may be received from the websites, with the individual's permission, and some data may come directly from a user's computing device as the user enters status updates, for example.

These non-clinical patient data provides a much more realistic and accurate depiction of the patient's overall holistic healthcare environment. Augmented with such non-clinical patient data, the analysis and predictive modeling performed by the present system to identify patients at high-risk of readmission or disease recurrence become much more robust and accurate.

The system 10 is further adapted to receive user preference and system configuration data from clinicians' computing devices (mobile devices, tablet computers, laptop computers, desktop computers, servers, etc.) 19 in a wired or wireless manner. These computing devices are equipped to display a system dashboard and/or another graphical user interface to present system data and reports. For example, a clinician (healthcare personnel) may immediately generate a list of patients that have the highest congestive heart failure risk scores, e.g., top n numbers or top x %. The graphical user interface are further adapted to receive the user's (healthcare personnel) input of preferences and configurations, etc. The data may be transmitted, presented, and displayed to the clinician/user in the form of web pages, web-based message, text files, video messages, multimedia messages, text messages, e-mail messages, and in a variety of suitable ways and formats.

As shown in FIG. 1, the clinical predictive and monitoring system 10 may receive data streamed real-time, or from historic or batched data from various data sources. Further, the system 10 may store the received data in a data store 20 or process the data without storing it first. The real-time and stored data may be in a wide variety of formats according to a variety of protocols, including CCD, XDS, HL7, SSO, HTTPS, EDI, CSV, etc. The data may be encrypted or otherwise secured in a suitable manner. The data may be pulled (polled) by the system 10 from the various data sources or the data may be pushed to the system 10 by the data sources. Alternatively or in addition, the data may be received in batch processing according to a predetermined schedule or on-demand. The data store 20 may include one or more local servers, memory, drives, and other suitable storage devices. Alternatively or in addition, the data may be stored in a data center in the cloud.

The computer system 12 may comprise a number of computing devices, including servers, that may be located locally or in a cloud computing farm. The data paths between the computer system 12 and the data store 20 may be encrypted or otherwise protected with security measures or transport protocols now known or later developed.

Figure 2:
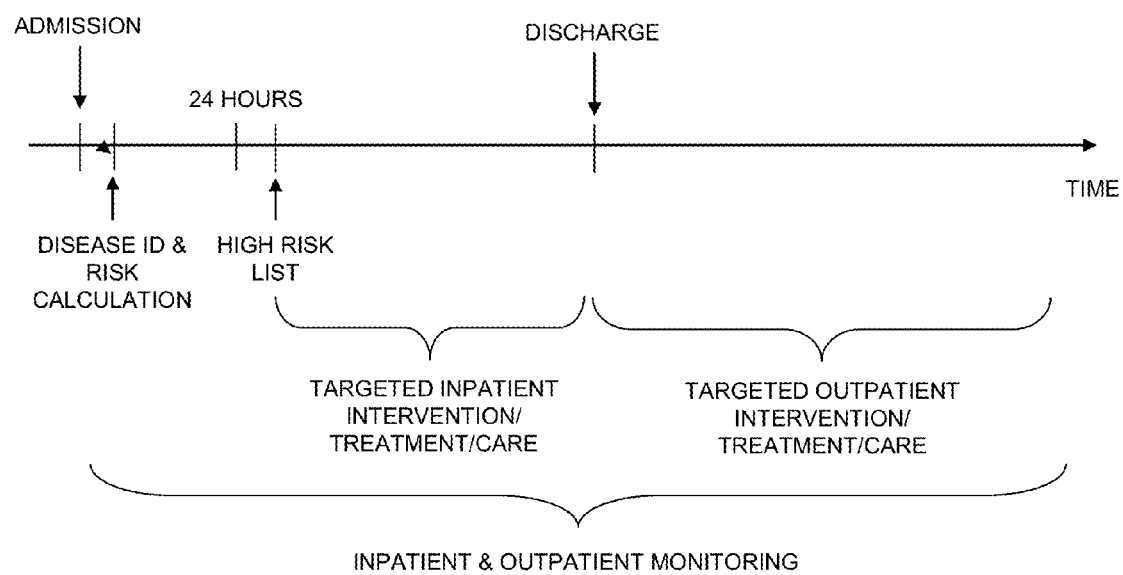
FIG. 2 is a timeline diagram of an exemplary embodiment of a clinical predictive and monitoring system and method according to the present disclosure.

FIG. 2 is a timeline diagram of an exemplary embodiment of a clinical predictive and monitoring system and method according to the present disclosure. The timeline diagram is used to illustrate how the clinical predictive and monitoring system and method 10 may be applied to reduce hospital readmission rate relating to congestive heart failure as an example. A majority of U.S. hospitals struggle to contain readmission rates related to congestive heart failure. Though numerous studies have found that some combination of careful discharge planning, care provider coordination, and intensive counseling can prevent subsequent re-hospitalizations, success is difficult to achieve and sustain at the typical U.S. hospital. Enrolling all heart failure patients into a uniform, high intensity care transition program requires a depth of case management resources that is out of reach for many institutions, particularly safety-net hospitals. The clinical predictive and monitoring system and method 10 is adapted to accurately stratify risk for certain diseases and conditions such as 30-day readmission among congestive heart failure patients.

Within 24 hours of a patient's admission to the hospital, stored historical and real-time data related to the patients are analyzed by the clinical predictive and monitoring system and method 10 to identify specific diseases and conditions related to the patient, such as congestive heart failure. Further, the system 10 calculates a risk score for congestive heart failure for this particular patient within 24 hours of admission. If this particular patient's risk score for congestive heart failure is above a certain risk threshold, then the patient is identified on a list of high-risk patients that is presented to an intervention coordination team. The processes for disease identification and risk score calculation are described in more detail below.

The clinical predictive and monitoring system and method 10 are operable to display, transmit, and otherwise present the list of high risk patients to the intervention coordination team, which may include physicians, physician assistants, case managers, patient navigators, nurses, social workers, family members, and other personnel or individuals involved with the patient's care. The means of presentment may include e-mail, text messages, multimedia messages, voice messages, web pages, facsimile, audible or visual alerts, etc. delivered by a number of suitable electronic or portable computing devices. The intervention coordination team may then prioritize intervention for the highest risk patients and provide targeted inpatient care and treatment. The clinical predictive and monitoring system and method 10 may further automatically present a plan to include recommended intervention and treatment options. Some intervention plans may include detailed inpatient clinical assessment as well as patient nutrition, pharmacy, case manager, and heart failure education consults starting early in the patient's hospital stay. The intervention coordination team may immediately conduct the ordered inpatient clinical and social interventions. Additionally, the plan may include clinical and social outpatient interventions and developing a post-discharge plan of care and support.

High-risk patients are also assigned a set of high-intensity outpatient interventions. Once a targeted patient is discharged, outpatient intervention and care begin. Such interventions may include a follow-up phone call within 48 hours from the patient's case manager, such as a nurse; doctors' appointment reminders and medication updates; outpatient case management for 30 days; a follow-up appointment in a clinic within 7 days of discharge; a subsequent cardiology appointment if needed; and a follow-up primary care visit. Interventions that have been found to be successful are based on well-known readmission reduction programs and strategies designed to significantly reduce 30-day readmissions associated with congestive heart failure.

The clinical predictive and monitoring system and method 10 continue to receive clinical and non-clinical data regarding the patient identified as high risk during the hospital stay and after the patient's discharge from the hospital to further improve the diagnosis and modify or augment the treatment and intervention plan, if necessary.

After the patient is discharged from the hospital, the clinical predictive and monitoring system and method 10 continue to monitor patient intervention status according to the electronic medical records, case management systems, social services entities, and other data sources as described above. The clinical predictive and monitoring system and method 10 may also interact directly with caregivers, case managers, and patients to obtain additional information and to prompt action. For example, the clinical predictive and monitoring system and method 10 may notify a physician that one of his or her patients has returned to the hospital, the physician can then send a pre-formatted message to the system directing it to notify a specific case management team. In another example, the clinical predictive and monitoring system and method 10 may recognize that a patient missed a doctor's appointment and hasn't rescheduled. The system may send the patient a text message reminding the patient to reschedule the appointment.

Figure 3:
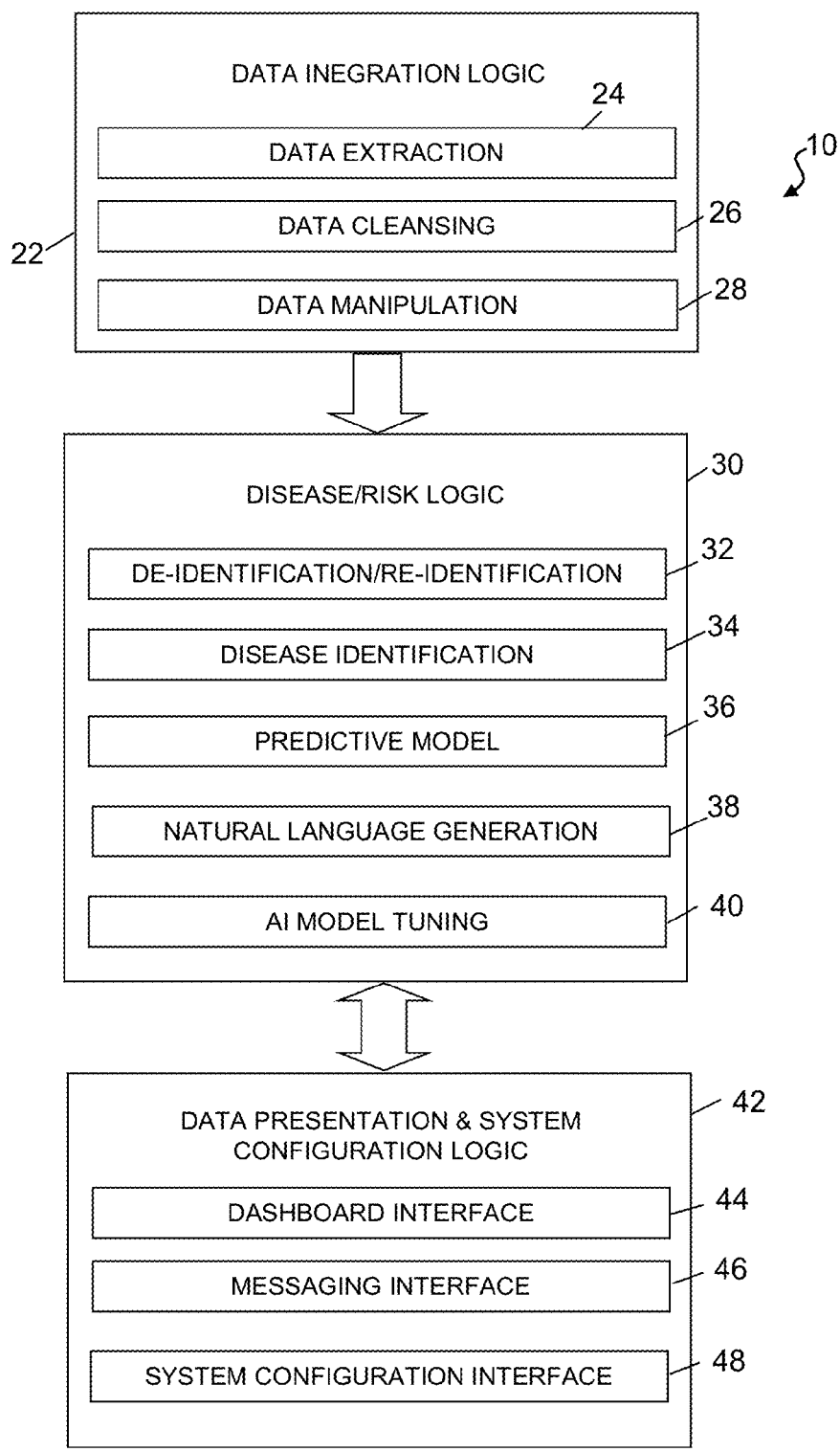
FIG. 3 is a simplified logical block diagram of an exemplary embodiment of a clinical predictive and monitoring system and method according to the present disclosure.

FIG. 3 is a simplified logical block diagram of an exemplary embodiment of a clinical predictive and monitoring system and method 10 according to the present disclosure. Because the system 10 receives and extracts data from many disparate sources in myriad formats pursuant to different protocols, the incoming data must first undergo a multi-step process before they may be properly analyzed and utilized. The clinical predictive and monitoring system and method 10 includes a data integration logic module 22 that further includes a data extraction process 24, a data cleansing process 26, and a data manipulation process 28. It should be noted that although the data integration logic module 22 is shown to have distinct processes 24-28, these are done for illustrative purposes only and these processes may be performed in parallel, iteratively, and interactively.

The data extraction process 24 extracts clinical and non-clinical data from data sources in real-time or in historical batch files either directly or through the Internet, using various technologies and protocols. Preferably in real-time, the data cleansing process 26 "cleans" or pre-processes the data, putting structured data in a standardized format and preparing unstructured text for natural language processing (NLP) to be performed in the disease/risk logic module 30 described below. The system may also receive "clean" data and convert them into desired formats (e.g., text date field converted to numeric for calculation purposes).

The data manipulation process 28 may analyze the representation of a particular data feed against a meta-data dictionary and determine if a particular data feed should be re-configured or replaced by alternative data feeds. For example, a given hospital EMR may store the concept of "maximum creatinine" in different ways. The data manipulation process 28 may make inferences in order to determine which particular data feed from the EMR would best represent the concept of "creatinine" as defined in the meta-data dictionary and whether a feed would need particular re-configuration to arrive at the maximum value (e.g., select highest value).

The data integration logic module 22 then passes the pre-processed data to a disease/risk logic module 30. The disease risk logic module 30 is operable to calculate a risk score associated with an identified disease or condition for each patient and identifying those patients who should receive targeted intervention and care. The disease/risk logic module 30 includes a de-identification/re-identification process 32 that is adapted to remove all protected health information according to HIPAA standards before the data is transmitted over the Internet. It is also adapted to re-identify the data. Protected health information that may be removed and added back may include, for example, name, phone number, facsimile number, email address, social security number, medical record number, health plan beneficiary number, account number, certificate or license number, vehicle number, device number, URL, all geographical subdivisions smaller than a State, including street address, city, county, precinct, zip code, and their equivalent geocodes (except for the initial three digits of a zip code, if according to the current publicly available data from the Bureau of the Census), Internet Protocol number, biometric data, and any other unique identifying number, characteristic, or code.

The disease/risk logic module 30 further includes a disease identification process 34. The disease identification process 34 is adapted to identify one or more diseases or conditions of interest for each patient. The disease identification process 34 considers data such as lab orders, lab values, clinical text and narrative notes, and other clinical and historical information to determine the probability that a patient has a particular disease. Additionally, during disease identification, natural language processing is conducted on unstructured clinical and non-clinical data to determine the disease or diseases that the physician believes are prevalent. This process 34 may be performed iteratively over the course of many days to establish a higher confidence in the disease identification as the physician becomes more confident in the diagnosis. New or updated patient data may not support a previously identified disease, and the system would automatically remove the patient from that disease list. The natural language processing combines a rule-based model and a statistically-based learning model.

The disease identification process 34 utilizes a hybrid model of natural language processing, which combines a rule-based model and a statistically-based learning model. During natural language processing, raw unstructured data, for example, physicians' notes and reports, first go through a process called tokenization. The tokenization process divides the text into basic units of information in the form of single words or short phrases by using defined separators such as punctuation marks, spaces, or capitalizations. Using the rule-based model, these basic units of information are identified in a meta-data dictionary and assessed according to predefined rules that determine meaning. Using the statistical-based learning model, the disease identification process 34 quantifies the relationship and frequency of word and phrase patterns and then processes them using statistical algorithms. Using machine learning, the statistical-based learning model develops inferences based on repeated patterns and relationships. The disease identification process 34 performs a number of complex natural language processing functions including text pre-processing, lexical analysis, syntactic parsing, semantic analysis, handling multi-word expression, word sense disambiguation, and other functions.

For example, if a physician's notes include the following: "55 yo m c h/o dm, cri. now with adib rvr, chfexac, and rle cellulitis going to 10W, tele." The data integration logic 22 is operable to translate these notes as: "Fifty-five-year-old male with history of diabetes mellitus, chronic renal insufficiency now with atrial fibrillation with rapid ventricular response, congestive heart failure exacerbation and right lower extremity cellulitis going to 10 West and on continuous cardiac monitoring."

Continuing with the prior example, the disease identification process 34 is adapted to further ascertain the following: 1) the patient is being admitted specifically for atrial fibrillation and congestive heart failure; 2) the atrial fibrillation is severe because rapid ventricular rate is present; 3) the cellulitis is on the right lower extremity; 4) the patient is on continuous cardiac monitoring or telemetry; and 5) the patient appears to have diabetes and chronic renal insufficiency.

The disease/risk logic module 30 further comprises a predictive model process 36 that is adapted to predict the risk of particular diseases or condition of interest according to one or more predictive models. For example, if the hospital desires to determine the level of risk for future readmission for all patients currently admitted with heart failure, the heart failure predictive model may be selected for processing patient data. However, if the hospital desires to determine the risk levels for all internal medicine patients for any cause, an all-cause readmissions predictive model may be used to process the patient data. As another example, if the hospital desires to identify those patients at risk for short-term and long-term diabetic complications, the diabetes predictive model may be used to target those patients. Other predictive models may include HIV readmission, diabetes identification, risk for cardiopulmonary arrest, kidney disease progression, acute coronary syndrome, pneumonia, cirrhosis, all-cause disease-independent readmission, colon cancer pathway adherence, and others.

Continuing to use the prior example, the predictive model for congestive heart failure may take into account a set of risk factors or variables, including the worst values for laboratory and vital sign variables such as: albumin, total bilirubin, creatine kinase, creatinine, sodium, blood urea nitrogen, partial pressure of carbon dioxide, white blood cell count, troponin-I, glucose, internationalized normalized ratio, brain natriuretic peptide, pH, temperature, pulse, diastolic blood pressure, and systolic blood pressure. Further, non-clinical factors are also considered, for example, the number of home address changes in the prior year, risky health behaviors (e.g., use of illicit drugs or substance), number of emergency room visits in the prior year, history of depression or anxiety, and other factors. The predictive model specifies how to categorize and weight each variable or risk factor, and the method of calculating the predicted probably of readmission or risk score. In this manner, the clinical predictive and monitoring system and method 10 is able to stratify, in real-time, the risk of each patient that arrives at a hospital or another healthcare facility. Therefore, those patients at the highest risks are automatically identified so that targeted intervention and care may be instituted. One output from the disease/risk logic module 30 includes the risk scores of all the patients for particular disease or condition. In addition, the module 30 may rank the patients according to the risk scores, and provide the identities of those patients at the top of the list. For example, the hospital may desire to identify the top 20 patients most at risk for congestive heart failure readmission, and the top 5% of patients most at risk for cardio-pulmonary arrest in the next 24 hours. Other diseases and conditions that may be identified using predictive modeling include, for example, HIV readmission, diabetes identification, kidney disease progression, colorectal cancer continuum screening, meningitis management, acid-base management, anticoagulation management, etc.

The disease/risk logic module 30 may further include a natural language generation module 38. The natural language generation module 38 is adapted to receive the output from the predictive model 36 such as the risk score and risk variables for a patient, and "translate" the data to present the evidence that the patient is at high-risk for that disease or condition. This module 30 thus provides the intervention coordination team additional information that supports why the patient has been identified as high-risk for the particular disease or condition. In this manner, the intervention coordination team may better formulate the targeted inpatient and outpatient intervention and treatment plan to address the patient's specific situation.

The disease/risk logic module 30 further includes an artificial intelligence (AI) model tuning process 40. The artificial intelligence model tuning process 38 utilizes adaptive self-learning capabilities using machine learning technologies. The capacity for self-reconfiguration enables the system and method 10 to be sufficiently flexible and adaptable to detect and incorporate trends or differences in the underlying patient data or population that may affect the predictive accuracy of a given algorithm. The artificial intelligence model tuning process 40 may periodically retrain a selected predictive model for improved accurate outcome to allow for selection of the most accurate statistical methodology, variable count, variable selection, interaction terms, weights, and intercept for a local health system or clinic. The artificial intelligence model tuning process 40 may automatically modify or improve a predictive model in three exemplary ways. First, it may adjust the predictive weights of clinical and non-clinical variables without human supervision. Second, it may adjust the threshold values of specific variables without human supervision. Third, the artificial intelligence model tuning process 40 may, without human supervision, evaluate new variables present in the data feed but not used in the predictive model, which may result in improved accuracy. The artificial intelligence model tuning process 40 may compare the actual observed outcome of the event to the predicted outcome then separately analyze the variables within the model that contributed to the incorrect outcome. It may then re-weigh the variables that contributed to this incorrect outcome, so that in the next reiteration those variables are less likely to contribute to a false prediction. In this manner, the artificial intelligence model tuning process 40 is adapted to reconfigure or adjust the predictive model based on the specific clinical setting or population in which it is applied. Further, no manual reconfiguration or modification of the predictive model is necessary. The artificial intelligence model tuning process 40 may also be useful to scale the predictive model to different health systems, populations, and geographical areas in a rapid timeframe.

As an example of how the artificial intelligence model tuning process 40 functions, the sodium variable coefficients may be periodically reassessed to determine or recognize that the relative weight of an abnormal sodium laboratory result on a new population should be changed from 0.1 to 0.12. Over time, the artificial intelligence model tuning process 38 examines whether thresholds for sodium should be updated. It may determine that in order for the threshold level for an abnormal sodium laboratory result to be predictive for readmission, it should be changed from, for example, 140 to 136 mg/dL. Finally, the artificial intelligence model tuning process 40 is adapted to examine whether the predictor set (the list of variables and variable interactions) should be updated to reflect a change in patient population and clinical practice. For example, the sodium variable may be replaced by the NT-por-BNP protein variable, which was not previously considered by the predictive model.

The results from the disease/risk logic module 30 are provided to the hospital personnel, such as the intervention coordination team, and other caretakers by a data presentation and system configuration logic module 42. The data presentation logic module 42 includes a dashboard interface 44 that is adapted to provide information on the performance of the clinical predictive and monitoring system and method 10. A user (e.g., hospital personnel, administrator, and intervention coordination team) is able to find specific data they seek through simple and clear visual navigation cues, icons, windows, and devices. The interface may further be responsive to audible commands, for example. Because the number of patients a hospital admits each day can be overwhelming, a simple graphical interface that maximizes efficiency and reduce user navigation time is desirable. The visual cues are preferably presented in the context of the problem being evaluated (e.g., readmissions, out-of-ICU, cardiac arrest, diabetic complications, among others).

The dashboard user interface 44 allows interactive requesting of a variety of views, reports and presentations of extracted data and risk score calculations from an operational database within the system. including, for example, summary views of a list of patient in a specific care location; detailed explanation of the components of the various sub-scores; graphical representations of the data for a patient or population over time; comparison of incidence rates of predicted events to the rates of prediction in a specified time frame; summary text clippings, lab trends and risk scores on a particular patient for assistance in dictation or preparation of history and physical reports, daily notes, sign-off continuity of care notes, operative notes, discharge summaries, continuity of care documents to outpatient medical practitioners; order generation to automate the generation of orders authorized by a local care providers healthcare environment and state and national guidelines to be returned to the practitioner's office, outside healthcare provider networks or for return to a hospital or practices electronic medical record; aggregation of the data into frequently used medical formulas to assist in care provision including but not limited to: acid-base calculation, MELD score, Child-Pugh-Turcot score, TIMI risk score, CHADS score, estimated creatinine clearance, Body Surface area, Body Mass Index, adjuvant, neoadjuvant and metastatic cancer survival nomograms, MEWS score, APACHE score, SWIFT score, NIH stroke scale, PORT score, AJCC staging; and publishing of elements of the data on scanned or electronic versions of forms to create automated data forms.

The data presentation and system configuration logic module 40 further includes a messaging interface 46 that is adapted to generate output messaging code in forms such as HL7 messaging, text messaging, e-mail messaging, multimedia messaging, web pages, web portals, REST, XML, computer generated speech, constructed document forms containing graphical, numeric, and text summary of the risk assessment, reminders, and recommended actions. The interventions generated or recommended by the system and method 10 may include: risk score report to the primary physician to highlight risk of readmission for their patients; score report via new data field input into the EMR for use by population surveillance of entire population in hospital, covered entity, accountable care population, or other level of organization within a healthcare providing network; comparison of aggregate risk of readmissions for a single hospital or among hospitals to allow risk-standardized comparisons of hospital readmission rates; automated incorporation of score into discharge summary template, continuity of care document (within providers in the inpatient setting or to outside physician consultants and primary care physicians), HL7 message to facility communication of readmission risk transition to nonhospital physicians; and communicate subcomponents of the aggregate social-environmental score, clinical score and global risk score. These scores would highlight potential strategies to reduce readmissions including: generating optimized medication lists; allowing pharmacies to identify those medication on formulary to reduce out-of-pocket cost and improve outpatient compliance with the pharmacy treatment plan; flagging nutritional education needs; identifying transportation needs; assessing housing instability to identify need for nursing home placement, transitional housing, Section 8 HHS housing assistance; identifying poor self regulatory behavior for additional follow-up phone calls; identifying poor social network scores leading to recommendation for additional in home RN assessment; flagging high substance abuse score for consultation of rehabilitation counselling for patients with substance abuse issues.

This output may be transmitted wirelessly or via LAN, WAN, the Internet, and delivered to healthcare facilities' electronic medical record stores, user electronic devices (e.g., pager, text messaging program, mobile telephone, tablet computer, mobile computer, laptop computer, desktop computer, and server), health information exchanges, and other data stores, databases, devices, and users. The system and method 10 may automatically generate, transmit, and present information such as high-risk patient lists with risk scores, natural language generated text, reports, recommended actions, alerts, Continuity of Care Documents, flags, appointment reminders, and questionnaires.

The data presentation and system configuration logic module 40 further includes a system configuration interface 48. Local clinical preferences, knowledge, and approaches may be directly provided as input to the predictive models through the system configuration interface 46. This system configuration interface 46 allows the institution or health system to set or reset variable thresholds, predictive weights, and other parameters in the predictive model directly. The system configuration interface 48 preferably includes a graphical user interface designed to minimize user navigation time.

Figure 4:
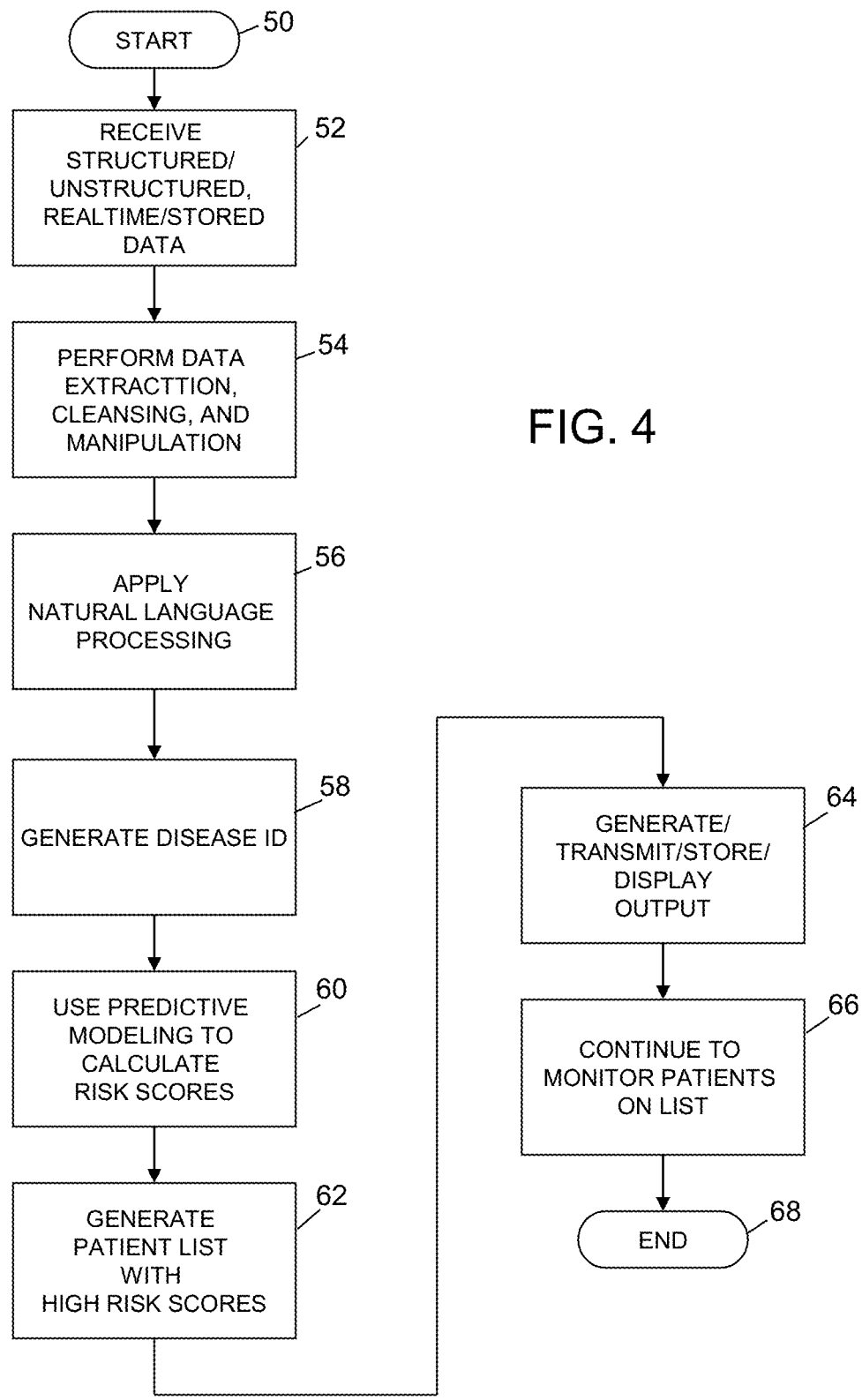
FIG. 4 is a simplified flowchart of an exemplary embodiment of a clinical predictive and monitoring method according to the present disclosure.

FIG. 4 is a simplified flowchart of an exemplary embodiment of a clinical predictive and monitoring method 50 according to the present disclosure. The method 50 receives structured and unstructured clinical and non-clinical data related to specific patients from a variety of sources and in a number of different formats, as shown in block 52. These data may be encrypted or protected using data security methods now known or later developed. In block 54, the method 50 pre-processes the received data, such as data extraction, data cleansing, and data manipulation. Other data processing techniques now known and later developed may be utilized. In block 56, data processing methods such as natural language processing and other suitable techniques may be used to translate or otherwise make sense of the data. In block 58, by analyzing the pre-processed data, one or more diseases or conditions of interest as related to each patient are identified. In block 60, the method 50 applies one or more predictive models to further analyze the data and calculate one or more risk scores for each patient as related to the identified diseases or conditions. In blocks 62 and 64, one or more lists showing those patients with the highest risks for each identified disease or condition are generated, transmitted, and otherwise presented to hospital personnel, such as members of an intervention coordination team. These lists may be generated on a daily basis or according to another desired schedule. The intervention coordination team may then prescribe and follow targeted intervention and treatment plans for inpatient and outpatient care. In block 66, those patients identified as high-risk are continually monitored while they are undergoing inpatient and outpatient care. The method 50 ends in block 68.

Not shown explicitly in FIG. 4 is the de-identification process, in which the data become disassociated with the patient's identity to comply with HIPAA regulations. The data can be de-coupled with the patient's identity whenever they are transmitted over wired or wireless network links that may be compromised, and otherwise required by HIPAA. The method 50 is further adapted to reunite the patient data with the patient's identity.

Figure 5:
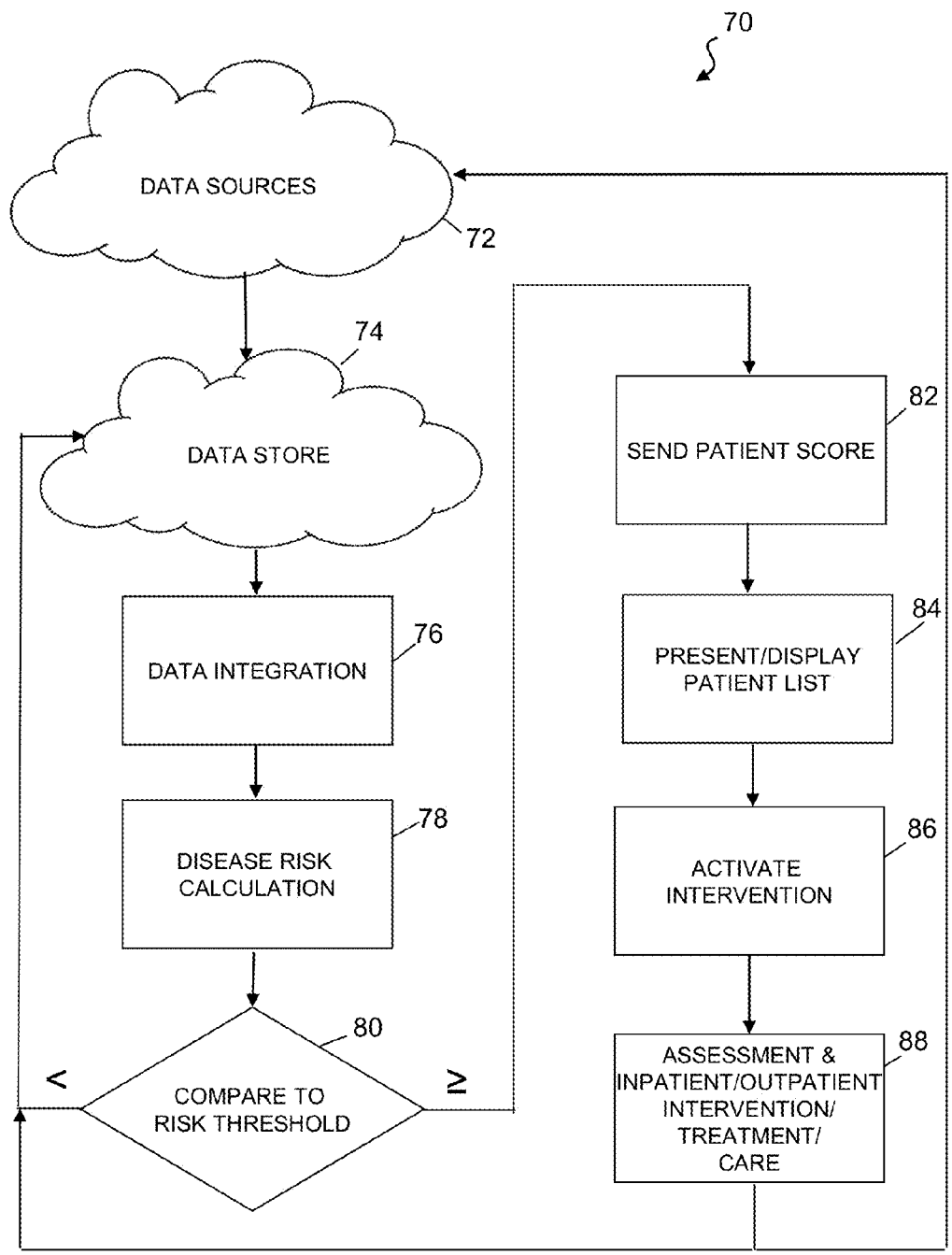
FIG. 5 is a simplified flowchart/block diagram of an exemplary embodiment of a clinical predictive and monitoring method according to the present disclosure.

FIG. 5 is a simplified flowchart/block diagram of an exemplary embodiment of a clinical predictive and monitoring method 70 according to the present disclosure. A variety of data are received from a number of disparate data sources 72 related to particular patients admitted at a hospital or a healthcare facility. The incoming data may be received in real-time or the data may be stored as historical data received in batches or on-demand. The incoming data are stored in a data store 74. In block 76, the received data undergo a data integration process (data extraction, data cleansing, data manipulation), as described above. The resultant pre-processed data then undergoes the disease logic process 78 during which de-identification, disease identification, and predictive modeling are performed. The risk score computed for each patient for a disease of interest is compared to a disease risk threshold in block 80. Each disease is associated with its own risk threshold. If the risk score is less than the risk threshold, then the process returns to data integration and is repeated when new data associated with a patient become available. If the risk score is greater than or equal to the risk threshold, then the identified patient having the high risk score is included in a patient list in block 82. In block 84, the patient list and other associated information may then be presented to the intervention coordination team in one or more possible ways, such as transmission to and display on a desktop or mobile device in the form of a text message, e-mail message, web page, etc. In this manner, an intervention coordination team is notified and activated to target the patients identified in the patient list for assessment, and inpatient and outpatient treatment and care, as shown in block 88. The process may thereafter provide feedback data to the data sources 72 and/or return to data integration 76 that continues to monitor the patient during his/her targeted inpatient and outpatient intervention and treatment. Data related to the patient generated during the inpatient and outpatient care, such as prescribed medicines and further laboratory results, radiological images, etc. is continually monitored according to pre-specified algorithms which define the patient's care plan.

Figure 6:
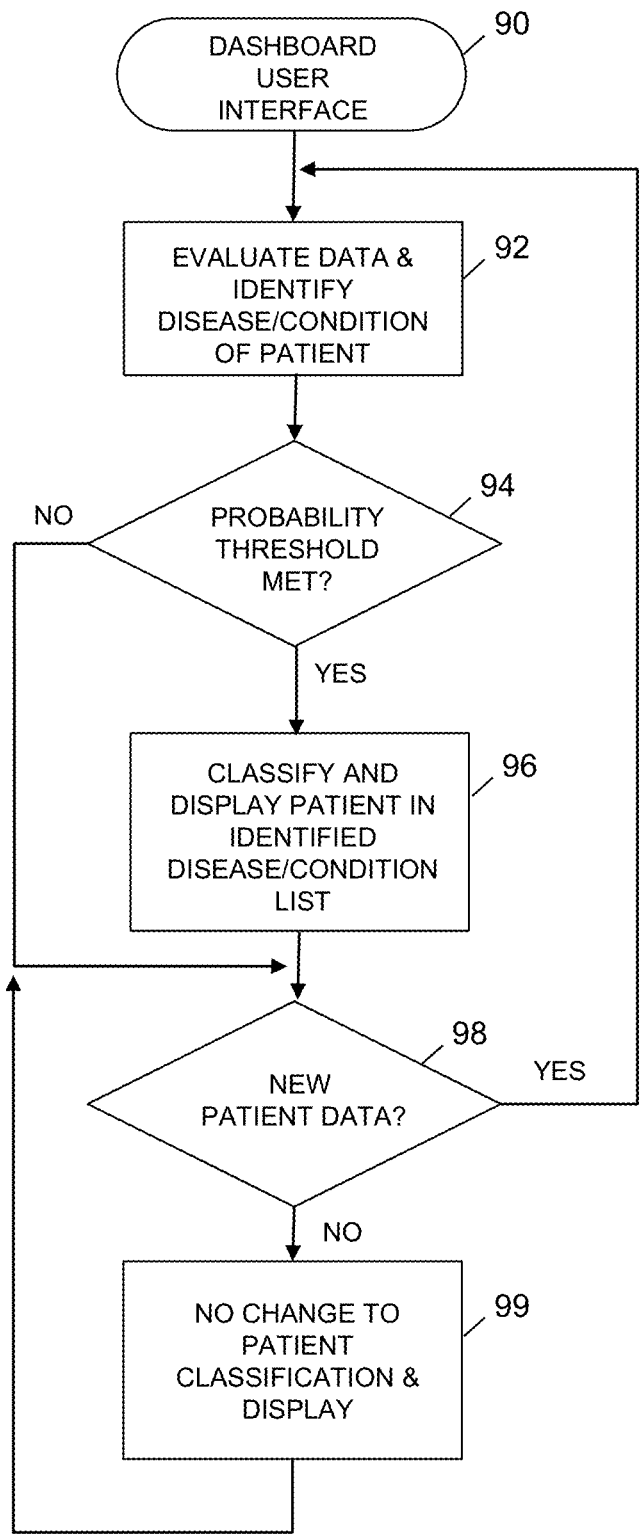
FIG. 6 is a simplified flowchart diagram of an exemplary embodiment of a dashboard user interface system and method according to the present disclosure.

FIG. 6 is a simplified flowchart diagram of an exemplary embodiment of a dashboard user interface system and method 90 according to the present disclosure. The patients' data are evaluated as described above, and those patients associated with targeted diseases and surveillance conditions are identified in block 92. The targeted diseases are those illnesses that the patient is at risk for readmission to the healthcare facility. The monitored conditions are those patient conditions, e.g., injury and harm, that are indicative of occurrence of adverse events in the healthcare facility. The patients' inclusion on a particular disease or surveillance condition list is further verified by comparison to a predetermined probability threshold, as shown in block 94. If the probability threshold is met, then the patient is classified or identified as belonging to a disease list or condition list. The display is also updated so that when a user selects a particular disease list for display, that patient is shown in the list, as shown in block 96. This may be seen in the exemplary screen in FIG. 8. In this exemplary screen, the list of patients that are at risk for 30-day readmission due to congestive heart failure (CHF) are identified and listed in the active congestive heart failure list. Details of the exemplary screen are provided below.

The user may print, transmit, and otherwise use the displayed information, and generate standard or custom reports. The reports may be primarily textual in nature, or include graphical information. For example, a graphical report may chart the comparison of expected to observed readmission rates for any disease type, condition, or category for patients enrolled or not enrolled in an intensive intervention program, the readmission rates for enrolled versus dropped patients over a period of time for any disease type, condition, or category. Patients with greater than 95%, for example, of probability of having heart failure, total versus enrolled over a specified time period, and the number of patients not readmitted within 30 day discharge readmission window by number of days from discharge. Additional exemplary standard tracking reports that may further identify all enrolled patients for which: post-discharge appointments are scheduled, post-discharge phone consults are scheduled, patient has attended follow-up appointment, patient has received post-discharge phone consult, patient has received and filled medical prescriptions, and patient has received transportation voucher. Further sample reports may include a comparison of expected to observed readmission rates for any disease type, event, or category for enrolled and not enrolled patients, readmission rates for enrolled vs. dropped patients over a period of time for any disease type, event, or category, patients with greater than 95% probability of having heart failure: total vs. enrolled over a specific time period, and the number of patients not readmitted within 30 day discharge readmission window by number of days from discharge. If the probability threshold is not met in block 94, then the patient's data are re-evaluated as new or updated data become available.

Another type of reports available are outcome optimization reports. These are reports designed to help users (administrators) assess the efficacy of a program, establish benchmarks, and identify needs for change on a systematic and population levels to improve care outcomes. The report may include data that assist in assessing the effectiveness of the identifying high risk patients. Some of the data may demonstrate effort spent, patients enrolled, and how often those patents truly are afflicted with the identified diseases. Reports may include data that assist in assessing whether interventions are given to the right patients, at the right time, etc.

As new, updated, or additional patient data become available, as shown in block 98, the data is evaluated to identify or verify disease/condition. The patient may be reclassified if the data now indicate the patient should be classified differently, for example. A patient may also be identified as an additional disease and be included in another list. For example, in the first 24 hours of admissions, the system identifies patient Jane Doe as having CHF. Upon receiving more information, such as lab results and new physician notes, the system identifies Jane Doe as also having AMI. Jane Doe will then be placed in the AMI list, and identified as an AMI patient as soon as the new diagnosis is available. Additionally, Jane Doe will remain in the CHF list, yet she will be identified as an AMI patient in that list.

If there is no new patient data, then there is no change to the patient classification and the display reflects the current state of patient classification, as shown in block 99. Accordingly, as real-time or near real-time patient data become available, the patients' disease and condition classification is re-evaluated and updated as necessary.

Figure 7:
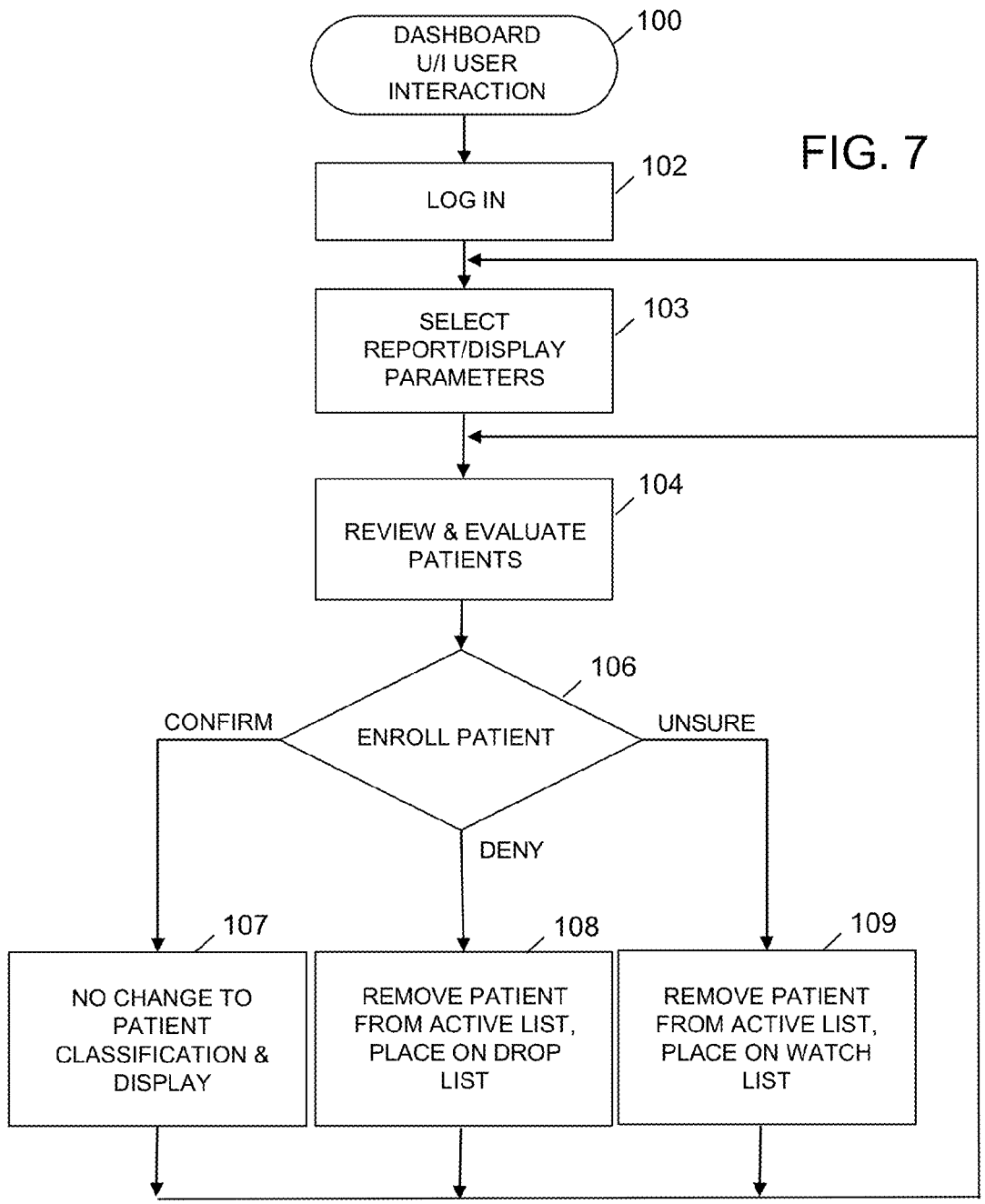
FIG. 7 is a simplified flowchart diagram of an exemplary embodiment of a typical user interaction with the dashboard user interface system and method according to the present disclosure.

FIG. 7 is a simplified flowchart diagram of an exemplary embodiment of a typical user interaction process 100 with the dashboard user interface system and method according to the present disclosure. All users that are permitted to access the system must have log-in security information such as username and password on record. All access to the system requires logging in to the system by supplying the correct log-in information, as shown in block 102. The user may select a number of parameters such as the disease type, event, risk level, and eligibility for high-intensity intervention care program enrollment to generate a report, as shown in block 103. The user may make this selection at any time after the login is successful. For example, the user may select a particular patient and review information associated with that patient. The user may then review and evaluate the displayed information, including clipped clinician notes, as shown in 104. The user may also print, transmit, or otherwise use, in some form, the displayed information.

Targeted predictive readmission diseases may include: congestive heart failure, pneumonia, acute myocardial infraction, diabetes, cardiopulmonary arrest and mortality, cirrhosis readmission, HIV readmission, sepsis, and all causes. Targeted disease identification may include: chronic kidney disease, sepsis, surveillance, chronic kidney disease in outpatient, diabetes mellitus in outpatient, and sepsis. Targeted conditions due to possible adverse event for surveillance may include: sepsis, post-operative pulmonary embolism (PE) or deep vein thrombosis (DVT), post-operative sepsis, post-operative shock, unplanned return to surgery, respiratory failure, hypertension, unexpected injury, inadequate communication, omission or errors in assessment, diagnosis, or monitoring, falls, hospital-acquired infections, medication-wrong patient, patent identification issues, out-of-ICU cardiopulmonary arrest and mortality, chronic kidney disease, shock, trigger for narcan, trigger for narcotic (over-sedation), trigger for hypoglycemia, and unexpected death.

The evaluation may include inputting comments about the patient, for example. As a part of the evaluation process, the user may confirm, deny, or express uncertainty about a patient's disease or condition identification or intervention program enrollment eligibility. For example, the user may review the notes and recommendations associated with a particular patient and confirm the inclusion of that patient in the congestive heart failure list, as shown in block 106. For example, the user reviews the clipped clinician's notes that call attention to key words and phrases, helping him or her find key information regarding disease identification by the system. Key terms such as "shortness of breath," "BNP was elevated," and "Lasix" help the user validate the disease identification of CHF for that patient. If the patient's classification, risk level, and eligibility level are confirmed, there is no change in the patient's classification and the data that are displayed (except to indicate this classification has been confirmed), as shown in block 107. The user may supply comments associated with the confirmation. User comments are stored and can be seen by other users in real-time or near real-time, allowing clear and timely communication between team members. The user may proceed to select a report or a display parameter in block 103, or review and evaluate patients in block 104.

Alternatively, the user may disagree with the inclusion of the patient in the congestive heart failure list, or express uncertainty. The user may enter comments explaining his or her assessment of and disagreement with the patient's disease identification. User comments are stored and can be seen by other users in real-time or near real-time, allowing clear and timely communication between team members.

If the user denies the classification, then the patient is removed from the active list of the target disease or condition, and placed on a drop list, as shown in block 108. In response to the user denying the classification, the system may additionally display or flag information about the patient that contributed to the inclusion of the patient on a particular list. For example, if the user denies the disease ID that John Smith has heart failure, the system may further display a query: "Mr. Smith likely has CHF due to the following factors: elevated BNP, shortness of breath, admitted for decompensated CHF 6/9. Are you sure you want to remove this patient from the active CHF list?" The user is required to respond to the query with yes or no. The system may additionally request rationale from the user for wanting to remove the patient from the active list. The rationale supplied by the user may be stored and displayed as reviewer comments. The user may also indicate uncertainty, and the patient is removed from the active list and placed on a watch list for further evaluation, as shown in block 109. The user may then review and evaluate additional patients on the same target disease list or review patients included on other disease and condition lists. At any point, the user may print, transmit, and otherwise use, in some form, the displayed information, such as generate standard or custom reports.

As an example, a patient Kit Yong Chen was identified as a CHF patient on admission. After receiving more data (i.e., new lab results and new physician notes) during her hospital stay, the system has identified this patient as having AMI.

The clinician notes upon admission states: 52 yo female w pmh of CAD, also with HTN presents with progressively worsening SOB and edema 1 month. 1. Dyspnea: likely CHF with elevated BNP afterload reduction with aCEi and diuresis with Lasix. O2 stats stable 2) elevated troponin: EKG with strain pattern follow serial enzymes to ROMI and cards consulted for possible Cath. The clinician notes thereafter states: 52 yo female with pmh of CAD, also with HTN presents with progressively worsening SOB and edema 1 month c CAD with LHC with stent prox LAD. 1. Elevated troponins—NSTEMI, despite pt denying CP—pt with known hx of CAD, mild troponin leak 0.13->0.15->0.09->0.1—on admission pt given 325, Plavix load with 300 mg 1, and heparin gtt—Metop increased 50 mg q6, possibly change Coreg at later time—LHC today per Cardiology, with PCI. also discuss with EP for possible ICD placement 2. Heart failure, acute on chronic—severe diastolic dysfunction be due HTN off meds+/−CAD—proBNP elevated 3183 on admission—initially started on lasix 40 tid, edema much improved, now on lasix 40 po bid—TTE completed showing: 4 chamber dilatation, RVH, nml LV thickness, severely depressed LVSF, LVEF 30%, mod MR, mild TR, AR and PR; severe diastolic dysfunction, RVSP 52—continue on Lasix, Lisinopril, Metop—discuss AICD evaluation with EP vs initial medical management.

The reviewer may assess the admission notes with the Disease ID of CHF compared with the second notes with PIECES Disease ID of AMI in an effort to validate this new real-time disease identification. The admission note indicated CHF as the primary disease. Key highlighted terms indicating CHF to a user include "pmh of CAD" (past medical history of coronary artery disease, "SOB" (shortness of breath), "edema," "elevated BNP." The second note indicates to a user that while the patient has CHF, CAD is the primary cause of the CHF. Key highlighted terms such as "elevated troponins" and "NSTEMI" (Non ST Segment Myocardial Infarction: heart attack) give the user a snapshot view of the key terms the system used to identify AMI as the primary disease. These highlighted key terms give the users the tools to validate in real-time or near real-time the system's change in disease identification. The user then confirms, denies, or expresses uncertainty with the new disease identification. In this example, the reviewer would assess the notes with the highlighted terms and validate the change by accepting the change in disease identification. Because the patient's main pathway of intervention would be for AMI, the patient, identified disease, and risk level would appear in the AMI list.

The dashboard user interface may also indicate a change in the level of risk. For example, upon return of lab results (slightly elevated creatinine and tox screen positive for cocaine) and other social factors that influence risk (noncompliance with sodium restriction due to homelessness) as well as medical pathway language queues, the system may identify this patient as high risk. A user can follow these changes in the real-time and to validate the change in risk level.

Figure 8:
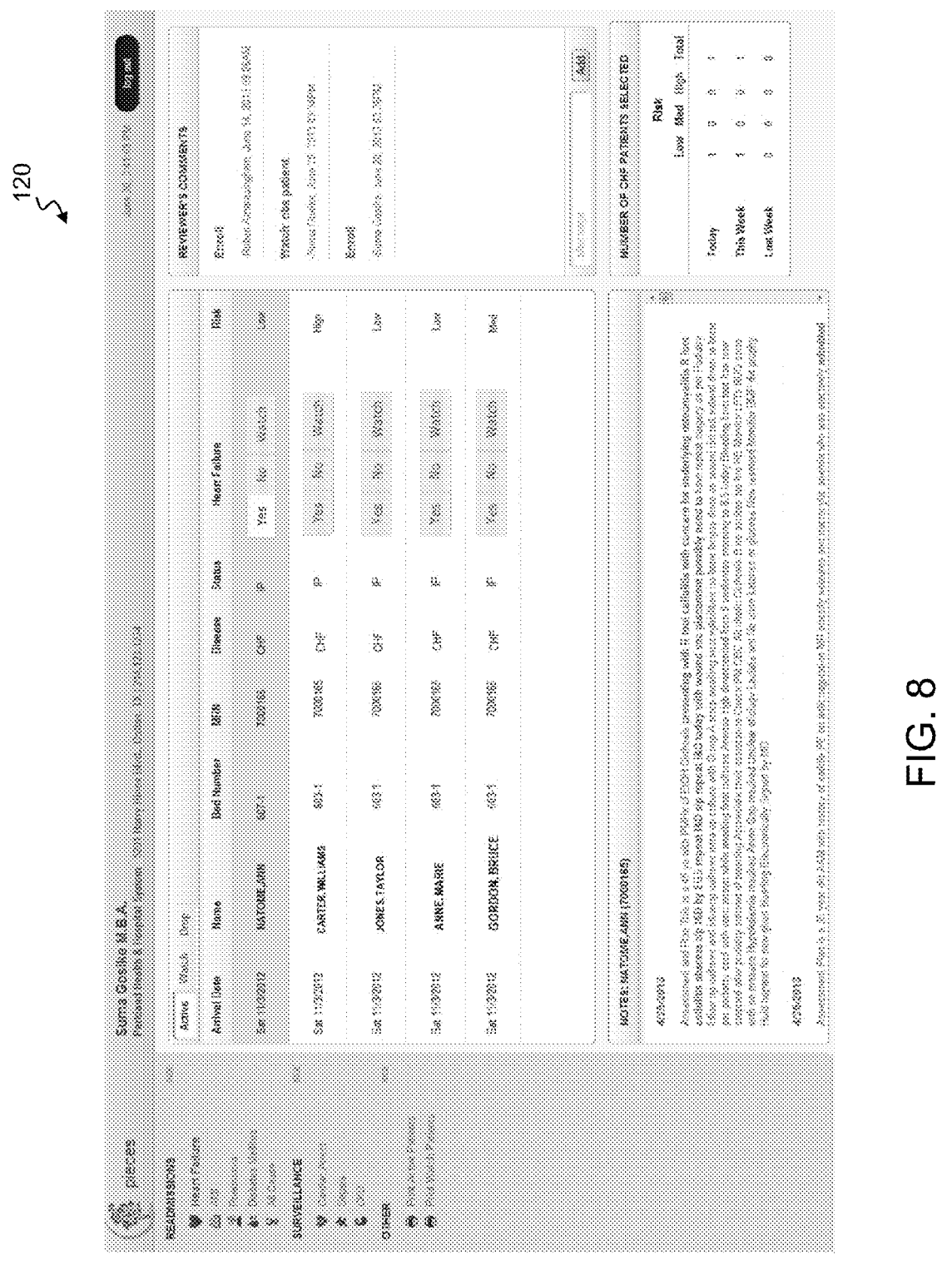

FIG. 8 is an exemplary screen shot 120 of a dashboard user interface system and method according to the present disclosure. The exemplary screen 120 shows a number of patients identified as having risk of readmission to the healthcare facility due to congestive heart failure. The exemplary screen shows the active congestive heart failure list. On the left hand side of the screen are target diseases and surveillance conditions that the user may select for review and evaluation. The target diseases are those diseases that the patients have been evaluated against that may put them at risk for readmission to the healthcare facility. Registries and surveillance conditions are those conditions that may be the result of adverse events occurring in the healthcare facility. Due to the space available to demonstrate the exemplary screen, only a select few diseases and conditions are shown, and it should be understood that the system and method is capable of evaluating and analyzing patient data for any number of target diseases and conditions. The dashboard user interface system is operable to organize and display patients belonging to a number of lists: active list (identified disease or condition), watch list (uncertainty), and drop list (denied). The user may click on any tab to view and print any list. A number of data items associated with each patient in a list are displayed, such as the admission or arrival date, patient name, identified target disease or condition, status (enrollment in intensive intervention program), whether the identified disease is confirmed, and the risk of readmission (expressed as, e.g., high, medium, or low). The type of data displayed for each list of patients may vary.

It should be noted that other types of data associated with each patient on the lists may be displayed as well such as the bed number and Medical record number (MRN) of each patient to transmit, and otherwise used to identify the patient. The exemplary screen 120 may also display the user's name and position (physician, case manager, RN, nurse practitioner, etc.) near the top of the screen. The numbers of patients at risk for heart failure that has been selected today, this week, and last week with the number of low, medium and high risk statistics are tabulated and further displayed on the exemplary screen.

The user may click on a particular patient displayed in a list, and obtain additional detailed information about that patient. For example, clipped clinician notes (patient's assessment and plan) are displayed near the bottom of the screen, with key words and phrases highlighted or otherwise emphasized to indicate those text that especially contributed to the inclusion of the patient in the identified target disease list, condition, risk level, and eligibility level. The user may scroll through all the clipped clinician notes associated with the patient, which are organized chronologically so that the user may review the progression of the disease, diagnosis, assessments, and pathways. Because the user can view the notes in real-time or near real-time, he or she is able to clinically validate the system's assessment of the unstructured text. The display further provide the reviewer's comments that are associated with the confirmation or denial of the disease or condition identification.

Not explicitly shown in FIG. 8 are additional features, such as a search bar to enable the user to enter one or more search criteria to locate one or more particular patients. For example, the user may input a medical record number, name, admission date, disease type, risk level, event, enrolled program, etc. to identify a set of patients that satisfy the search criteria. The search criteria may be based on other types of criteria, such as those patients that have missed their post-discharge appointments.

Figure 9:
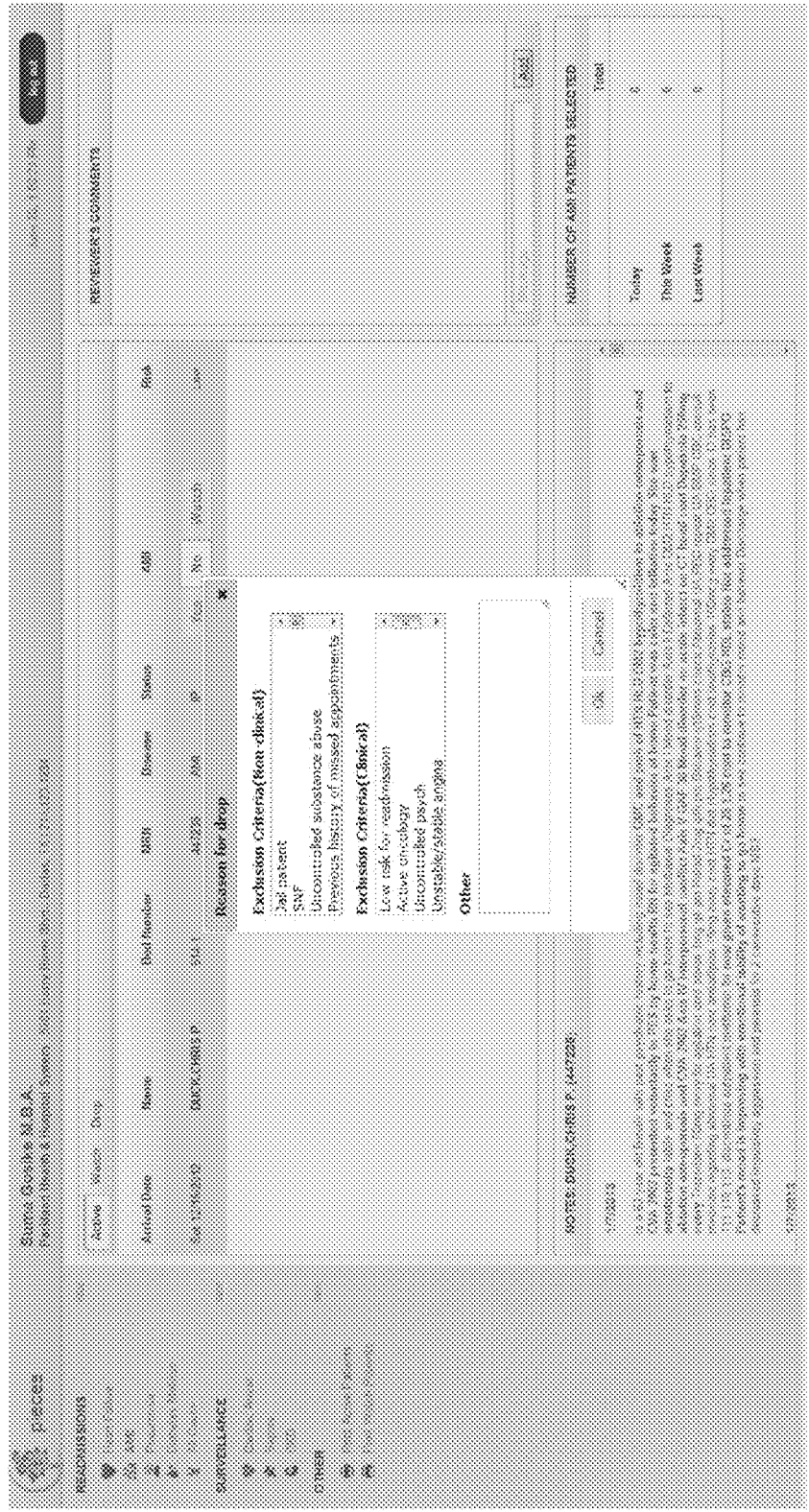
FIG. 9 is an exemplary screen shot of a dashboard user interface system and method showing a drop comment window according to the present disclosure.
Figure 10:
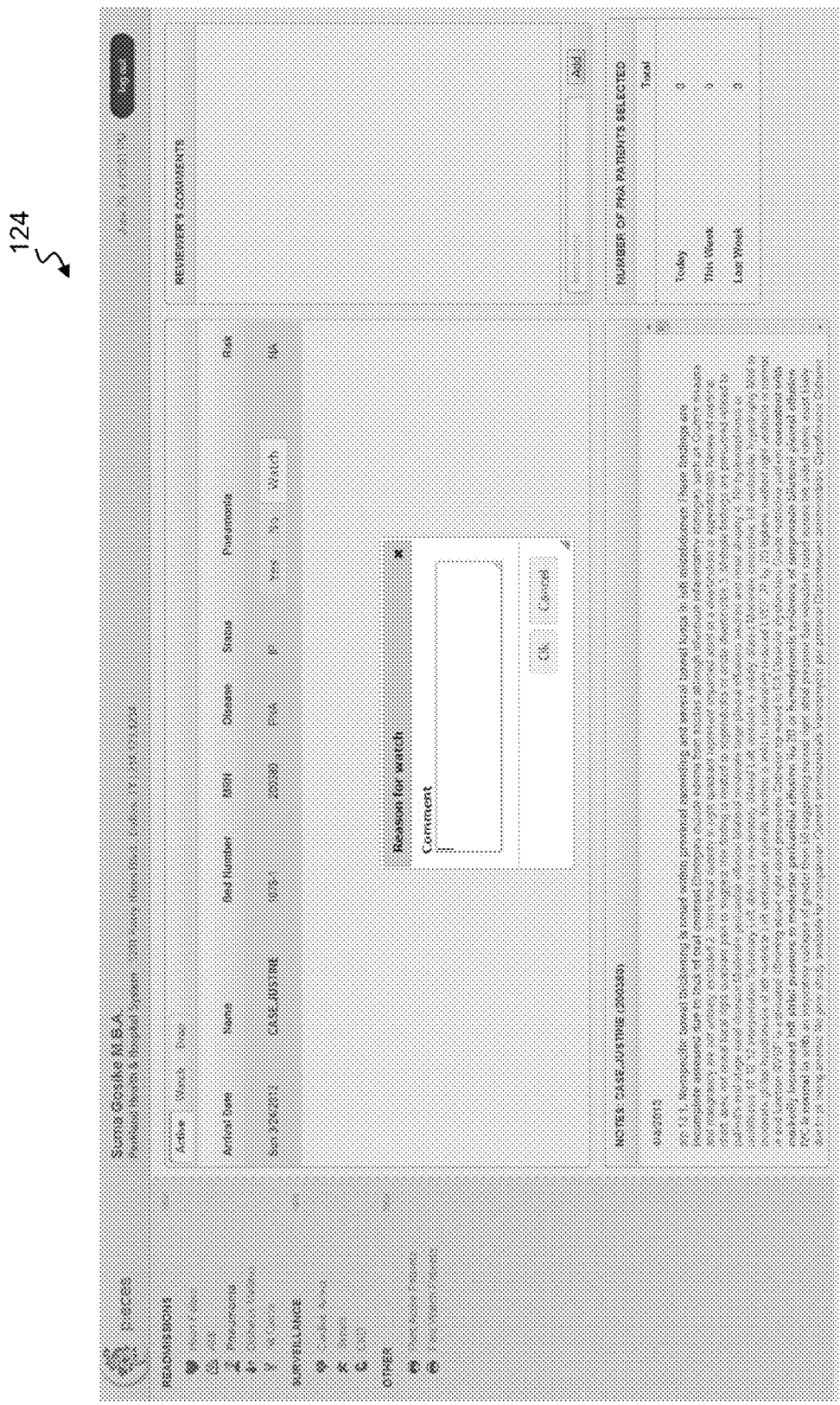
FIG. 10 is an exemplary screen shot of a dashboard user interface system and method showing a watch comment window according to the present disclosure.

FIGS. 9 and 10 are exemplary screen shots 122 and 124 of a dashboard user interface system and method showing a drop comment window and a watch comment window, respectively. If a user clicks on "No" to indicate the a particular patient should not be on the disease list, a reason for drop window pops up to enable the user to select clinical and non-clinical criteria that support the decision to deny the patient's classification on the AMI list. The user may further input reasons not already displayed. Similarly, the user may enter reasons that express uncertainty about a particular patient's inclusion on the pneumonia list, as the example shown in FIG. 10.

The display may optionally further include recommendations and reminders generated by the system. These recommendations and reminders may suggest evidence-based intervention options that would provide the greatest health benefit to the patient. The proposed intervention may consider clinical and nonclinical patient variables. In addition, previous patient enrollment results are factored into the recommended intervention. The orders for post-discharge care, e.g., nutrition, pharmacy, etc., may be automatically placed when a patient is enrolled in the program.

The system as described herein is operable to harness, simplify, sort, and present patient information in real-time or near real-time, predict and identify highest risk patients, identify adverse events, coordinate and alert practitioners, and monitor patient outcomes across time and space. The present system improves healthcare efficiency, assists with resource allocation, and presents the crucial information that lead to better patient outcomes.

The features of the present invention which are believed to be novel are set forth below with particularity in the appended claims. However, modifications, variations, and changes to the exemplary embodiments described above will be apparent to those skilled in the art, and the system and method described herein thus encompasses such modifications, variations, and changes and are not limited to the specific embodiments described herein.

What is claimed is:

1. A dashboard user interface method comprising:
displaying a navigable list of at least one target disease;
displaying a navigable list of patient identifiers associated with a target disease selected in the target disease list;
displaying historic and current data associated with a patient in the patient list identified as being associated with the selected target disease, including clinician notes at admission;
receiving, storing, and displaying review's comments; and
displaying automatically-generated intervention and treatment recommendations.

2. The dashboard user interface method of claim 1, wherein displaying the historic and current data further comprises displaying real-time or near real-time clinician notes.

3. The dashboard user interface method of claim 1, wherein displaying the historic and current data further comprises displaying clinician notes during hospital stay.

4. The dashboard user interface method of claim 1, wherein displaying the patient identifiers comprises displaying the patient names and medical record numbers.

5. The dashboard user interface method of claim 1, further comprising displaying a navigable list of information associated with patients including patient names, admission dates, identified target disease, risk level, and whether the disease identification is confirmed.

6. The dashboard user interface method of claim 1, further comprising displaying, to a reviewer, a query requesting confirming or denying a disease identification.

7. The dashboard user interface method of claim 1, wherein displaying clinician notes comprises displaying clinician notes with emphasized key words that contribute to the disease identification.

8. The dashboard user interface method of claim 1, wherein displaying a navigable list of patients associated with at least one target disease comprises displaying patients with patient data analyzed by a risk logic module operable to apply a predictive model to the patient data to determine at least one risk score associated with the at least one of the target diseases and identify at least one high-risk patient for the at least one of the target diseases, the predictive model including a plurality of weighted risk variables and risk thresholds in consideration of the clinical and non-clinical data to identify at least one high-risk patient associated with at least one of the target diseases.

9. The dashboard user interface method of claim 1, further comprising generating and transmitting information in a form selected from at least one member of the group consisting of reports, graphical data, text message, multimedia message, instant message, voice message, e-mail message, web page, web-based message, web pages, web-based message, and text files.

10. The dashboard user interface method of claim 1, further comprising generating and transmitting notification and information to at least one mobile device.

11. The dashboard user interface method of claim 1, further comprising displaying a navigable list of at least one condition associated with adverse events, and displaying a navigable list of patient identifiers associated with at least one condition.

12. The dashboard user interface method of claim 1, further comprising displaying at least one of an active list, drop list, watch list, and discharged list associated with a target disease.

13. A dashboard user interface method comprising:
displaying a navigable list of at least one target disease;
displaying a navigable list of at least one condition associated with adverse events;
displaying a navigable list of patients identifiers associated with a target disease selected in the target disease list;
displaying data associated with a patient in the patient list identified as being associated with the selected target disease, including clinician notes with highlighted text that contributed to the association with the selected target disease; and
receiving, storing, and displaying review's comments, including rationale for confirming, denying, or expressing uncertainty about the association with the selected target disease.

14. The dashboard user interface method of claim 13, further comprising displaying clinician notes in real-time or near real-time.

15. The dashboard user interface method of claim 13, further comprising displaying historic and current clinician notes during hospital stay.

16. The dashboard user interface method of claim 13, wherein displaying the patient identifiers comprises displaying the patient names.

17. The dashboard user interface method of claim 13, further comprising displaying a navigable list of information associated with patients including patient names, admission dates, identified target disease, risk level, and whether the disease identification is confirmed.

18. The dashboard user interface method of claim 13, further comprising displaying, to a reviewer, a query requesting confirming or denying a disease identification.

19. The dashboard user interface method of claim 13, wherein displaying clinician notes comprises displaying clinician notes with emphasized key words that contribute to the disease identification.

20. The dashboard user interface method of claim 13, wherein displaying a navigable list of patients associated with at least one target disease comprises displaying patients with patient data analyzed by a risk logic module operable to apply a predictive model to the patient data to determine at least one risk score associated with the at least one of the target diseases and identify at least one high-risk patient for the at least one of the target diseases, the predictive model including a plurality of weighted risk variables and risk thresholds in consideration of the clinical and non-clinical data to identify at least one high-risk patient associated with at least one of the target diseases.

21. The dashboard user interface method of claim 13, further comprising generating and transmitting information in a form selected from at least one member of the group consisting of reports, graphical data, text message, multimedia message, instant message, voice message, e-mail message, web page, web-based message, web pages, web-based message, and text files.

22. The dashboard user interface method of claim 13, further comprising generating and transmitting notification and information to at least one mobile device.

* * * * *